US008110707B2

(12) United States Patent
Iwase et al.

(10) Patent No.: US 8,110,707 B2
(45) Date of Patent: Feb. 7, 2012

(54) SURFACTANT

(75) Inventors: Toshiaki Iwase, Nishio (JP); Jun Kuroiwa, Okazaki (JP); Masanori Yoshida, Ibaraki (JP); Katsuya Uenishi, Osaka (JP); Kouei Murayama, Daito (JP)

(73) Assignees: Aisin AW Co., Ltd., Anjo-shi, Aichi (JP); Chuo Chemical Co., Ltd., Higashiosaka-shi, Osaka (JP)

( * ) Notice: Subject to any disclaimer, the term of this patent is extended or adjusted under 35 U.S.C. 154(b) by 289 days.

(21) Appl. No.: 12/444,987

(22) PCT Filed: Dec. 12, 2008

(86) PCT No.: PCT/JP2008/072708
§ 371 (c)(1), (2), (4) Date: Nov. 4, 2009

(87) PCT Pub. No.: WO2009/078369
PCT Pub. Date: Jun. 25, 2009

(65) Prior Publication Data

US 2010/0191014 A1 Jul. 29, 2010

(30) Foreign Application Priority Data

Dec. 14, 2007 (JP) ................................ 2007-322813

(51) Int. Cl.
*C07C 211/00* (2006.01)

(52) U.S. Cl. ......................... 564/286; 564/285; 564/292

(58) Field of Classification Search .................. 564/285, 564/286, 292
See application file for complete search history.

(56) References Cited

U.S. PATENT DOCUMENTS 4,678,605 A 7/1987 Geke et al.

FOREIGN PATENT DOCUMENTS

| | | | |
|---|---|---|---|
| JP | 61-106544 | | 5/1986 |
| JP | 61106544 | * | 5/1986 |
| JP | 61-192330 | * | 8/1986 |
| JP | 06-293896 | | 10/1994 |
| JP | 6293896 | * | 10/1994 |
| JP | 2005-187622 | | 7/2005 |

OTHER PUBLICATIONS

International Preliminary Report on Patentability dated Sep. 2, 2010, for International application No. PCT/JP2008/072708.
International Search Report mailed Feb. 10, 2009 in PCT/JP2008/072708 filed Dec. 12, 2008.

* cited by examiner

*Primary Examiner* — Deborah D Carr
(74) *Attorney, Agent, or Firm* — Drinker Biddle & Reath LLP

(57) ABSTRACT

A fatty acid salt of an alkyl quaternary ammonium is used as a novel surfactant which is a cationic surfactant having high detergency and low foaming property.

4 Claims, No Drawings

SURFACTANT

CROSS REFERENCE TO RELATED APPLICATIONS

This application is the National Stage of International Application No. PCT/JP2008/072708 filed Dec. 12, 2008, and claims benefit of Japanese Application No. 2007-322813 filed Dec. 14, 2007, both of which are herein incorporated by reference in their entirety.

TECHNICAL FIELD

The present invention relates to a novel surfactant including a quaternary ammonium salt.

BACKGROUND ART

A surfactant is generally used for washing metal members or the like, as a wash fluid mixed with, for example, a chelating agent, an alkaline agent and the like, in water. In this case, the surfactant removes oil smudge adhered to a surface of a metal member, by aggregating around the smudge to form a micelle that encloses the smudge, and diffusing through the fluid. The chelating agent enhances a washing effect by dissolving an oxide film present at an interface between a clean surface of the metal member and the smudge, into the wash fluid. The alkaline agent enhances detergency by interacting with the surfactant, and improves wettability, permeability and the like of the smudge to the wash fluid, by solubilizing the smudge through a reaction in the wash fluid to disperse the smudge, as well as by reducing a critical micelle concentration and surface tension of the surfactant.

In general, the surfactant is classified into anionic surfactant, cationic surfactant, nonionic surfactant, and ampholytic surfactant. Among these, the anionic surfactant and the ampholytic surfactant exhibit detergency, and used as a main component of the wash fluid. On the other hand, the cationic surfactant has a higher affinity with oil, and accordingly, in washing metal members or the like, the cationic surfactant is used together with a wash fluid containing the anionic surfactant, the ampholytic surfactant or the like, in order to prevent oil from being solubilized and emulsified in the wash fluid, and in the case of the wash fluid in an emulsified state, to decompose emulsified matters, so that the detergency of the wash fluid lasts for a long time period. For such a cationic surfactant, a quaternary ammonium salt has been known (see, for example, Patent documents 1 and 2).

Patent document 1: JP6-293896A
Patent document 2: JP2005-187622A

DISCLOSURE OF THE INVENTION

However, in the conventional wash fluid, there is a problem that foam of the wash fluid is formed which eventually overflows a washing container or the like. Especially in washing metal members or the like, a spray washing is adopted, in which case the surface of the metal member is covered with foam, which may reduce the washing effect. In addition, after washing, when the wash fluid is dropped from the surface of the metal member, foam may be formed in a reservoir or the like. Moreover, in the case of spray washing with which no water washing process is performed after washing, there is a problem that wash residues tend to remain on a surface of the washed substance, such as metal member.

On the other hand, in washing metal members, the conventional cationic surfactant, such as a quaternary ammonium salt, is typically used as an auxiliary additive for the ampholytic surfactant and the like, and thus the cationic surfactant itself has not been required to have detergency.

The present invention was made with the view toward solving the above-mentioned problems, and the object is to provide a novel surfactant which is a cationic surfactant with high detergency and low foaming property.

The surfactant of the present invention for attaining the above-described object is characterized by being represented by the following formula (1):

(1)

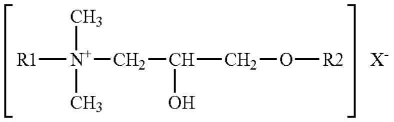

(where R1 is an alkyl group having a carbon number of 6-10 or a benzyl group,
R2 is a hydrogen atom, a methyl group, a benzyl group, or a substituent represented by the following formula (2):

(2)

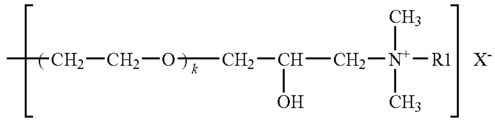

$X^-$ is a fatty acid ion having a carbon number of 6-10, and k is an integer of 0-22).

According to this configuration, by using the surfactant represented by the formula (1) as a wash fluid, washing can be performed with high detergency, while suppressing foaming.

The surfactant represented by the formula (1) is a cationic surfactant which can prevent oil from being solubilized and emulsified in the wash fluid, and thus detergency of the wash fluid can last for a long time period.

In the surfactant of the present invention, R1 is preferably an n-hexyl group, an n-octyl group, or an n-decyl group.

In the surfactant of the present invention, $X^-$ is preferably a caproate ion, a caprylate ion, or a caprate ion.

The surfactant of the present invention is especially suitable as a composition for spray washing.

BEST MODE FOR CARRYING OUT THE INVENTION

The surfactant of the present invention (hereinafter, frequently and simply referred to as "present surfactant") is a fatty acid salt of an alkyl quaternary ammonium (hereinafter, frequently and simply referred to as "quaternary ammonium salt") represented by the following formula (1):

(1)

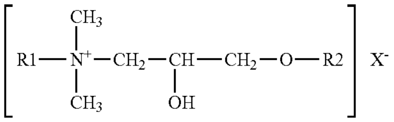

(where R1 is an alkyl group having a carbon number of 6-10 or a benzyl group,

R2 is a hydrogen atom, a methyl group, a benzyl group or a substituent represented by the following formula (2):

(2)

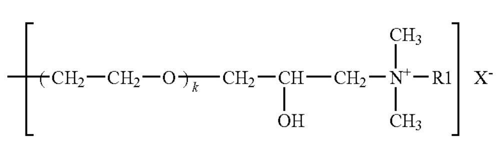

$X^-$ is a fatty acid ion having a carbon number of 6-10, and k is an integer of 0-22).

For R1 and $X^-$ in the formula (1), the following moieties can be mentioned.

Examples of the alkyl group having a carbon number of 6-10 represented by R1 include: an n-hexyl group, a structural isomer of a hexyl group such as 1,2-dimethylbutyl group, an n-heptyl group, a structural isomer of a heptyl group such as 1-methylhexyl group, an n-octyl group, a structural isomer of an octyl group such as 2-ethylhexyl group, an n-nonyl group, a structural isomer of a nonyl group such as 1,2,3-trimethylhexyl group, an n-decyl group, and a structural isomer of a decyl group such as 1,2-diethylhexyl group.

Examples of the fatty acid ion having a carbon number of 6-10 represented by include: a caproate ion (hexanoate ion), a structural isomer of a caproate ion such as 2,2-dimethylbutyrate ion, an enanthate ion (heptanoate ion), a structural isomer of an enanthate ion such as 2-methylcaproate ion, a caprylate ion (octanoate ion), a structural isomer of a caprylate ion such as 2-ethylcaproate ion, a pelargonate ion (nonanoate ion), a structural isomer of a pelargonate ion such as 3-methylcaprylate ion, a caprate ion (decanoate ion), and a structural isomer of a caprate ion such as 2,3-dimethylcaprylate ion. The fatty acid ion is not limited to a saturated fatty acid ion, and an unsaturated fatty acid ion may be used.

As illustrative embodiments of the quaternary ammonium salt represented by the formula (1), the following ammonium salts can be mentioned:

an ammonium salt of the formula (1) where R1 is an alkyl group having a carbon number of 6-10 or a benzyl group, an ammonium salt of the formula (1) where R1 is an n-hexyl group, an n-octyl group, or an n-decyl group, an ammonium salt of the formula (1) where R2 is a hydrogen atom, a methyl group, a benzyl group, or a substituent represented by the formula (2), an ammonium salt of the formula (1) where R2 is a methyl group or a substituent represented by the formula (2), an ammonium salt of the formula (1) where R2 is a substituent represented by the formula (2) and k is any of 0-22, an ammonium salt of the formula (1) where R2 is a substituent represented by the formula (2) and k is any of 1-4, an ammonium salt of the formula (1) where R2 is a substituent represented by the formula (2) and k is 1 or 2, an ammonium salt of the formula (1) where R1 is an n-hexyl group, an n-octyl group, or an n-decyl group, and R2 is a methyl group or a substituent represented by the formula (2) and k is 1 or 2, an ammonium salt of the formula (1) where $X^-$ is a caproate ion, a caprylate ion or a caprate ion, and an ammonium salt of the formula (1) where R1 is an n-hexyl group, an n-octyl group or an n-decyl group, R2 is a methyl group or a substituent represented by the formula (2) and k is 1 or 2, and $X^-$ is a caproate ion, a caprylate ion, or a caprate ion.

It should be noted that, in the formula (1), when R2 is a substituent represented by the formula (2), the present surfactant exhibits both cationic (positive ion) property and nonionic property. A degree of nonionic property depends on the number k, and nonionic property becomes stronger when k is larger. In the present surfactant, when k becomes larger, water solubility becomes higher, which enables a fatty acid ion having a high carbon number to be used as a counterion. However with a larger k, cationic property becomes weaker, which leads to lowering in detergency, oil separating property, and a pH buffering effect. Accordingly, k is set in a range of from 0 to 22.

Next, specific examples of the quaternary ammonium forming the quaternary ammonium salt represented by the formula (1) will be described below.

Examples of the alkyl quaternary ammonium of the formula (1) where R2 is a hydrogen atom include: 2,3-dihydroxypropyldimethylhexylammonium, 2,3-dihydroxypropyldimethyl-2-ethylhexylammonium, 2,3-dihydroxypropyldimethyloctylammonium, 2,3-dihydroxypropyldimethyldecylammonium, and 2,3-dihydroxypropyldimethylbenzylammonium.

Examples of the alkyl quaternary ammonium of the formula (1) where R2 is a methyl group include: 3-methoxy-2-hydroxypropyldimethylhexylammonium, 3-methoxy-2-hydroxypropyldimethyl-2-ethylhexylammonium, 3-methoxy-2-hydroxypropyldimethyloctylammonium, 3-methoxy-2-hydroxypropyldimethyldecylammonium, and 3-methoxy-2-hydroxypropyldimethylbenzylammonium.

Examples of the alkyl quaternary ammonium of the formula (1) where R2 is a benzyl group include: 3-benzyloxy-2-hydroxypropyldimethylhexylammonium, 3-benzyloxy-2-hydroxypropyldimethyl-2-ethylhexylammonium, 3-benzyloxy-2-hydroxypropyldimethyloctylammonium, 3-benzyloxy-2-hydroxypropyldimethyldecylammonium, and 3-benzyloxy-2-hydroxypropyldimethylbenzylammonium.

Examples of the alkyl quaternary ammonium of the formula (1) where R2 is a substituent represented by the formula (2) and k is 1 include: 3,3'-oxyethyleneoxy-bis(2-hydroxypropyldimethylhexylammonium), 3,3'-oxyethyleneoxy-bis(2-hydroxypropyldimethyl-2-ethylhexylammonium), 3,3'-oxyethyleneoxy-bis(2-hydroxypropyldimethyloctylammonium), 3,3'-oxyethyleneoxy-bis(2-hydroxypropyldimethyldecylammonium), and 3,3'-oxyethyleneoxy-bis(2-hydroxypropyldimethylbenzylammonium).

Examples of the alkyl quaternary ammonium of the formula (1) where R2 is a substituent represented by the formula (2) and k is 2 include: 3,3'-di(oxyethylene)oxy-bis(2-hydroxypropyldimethylhexylammonium), 3,3'-di(oxyethylene)oxy-bis(2-hydroxypropyldimethyl-2-ethylhexylammonium), 3,3'-di(oxyethylene)oxy-bis(2-hydroxypropyldimethyloctylammonium), 3,3'-di(oxyethylene)oxy-bis(2-hydroxypropyldimethyldecylammonium), and 3,3'-di(oxyethylene)oxy-bis(2-hydroxypropyldimethylbenzylammonium).

Examples of the alkyl quaternary ammonium of the formula (1) where R2 is a substituent represented by the formula (2) and k is 4 include: 3,3'-tetra(oxyethylene)oxy-bis(2-hydroxypropyldimethylhexylammonium), 3,3'-tetra(oxyethylene)oxy-bis(2-hydroxypropyldimethyl-2-ethylhexylammonium), 3,3'-tetra(oxyethylene)oxy-bis(2-hydroxypropyldimethyloctylammonium), 3,3'-tetra(oxyethylene)oxy-bis(2-hydroxypropyldimethyldecylammonium), and 3,3'-tetra(oxyethylene)oxy-bis(2-hydroxypropyldimethylbenzylammonium).

Examples of the alkyl quaternary ammonium of the formula (1) where R2 is a substituent represented by the formula (2) and k is 9 include: 3,3'-nona(oxyethylene)oxy-bis(2-hydroxypropyldimethylhexylammonium), 3,3'-nona(oxyethylene)oxy-bis(2-hydroxypropyldimethyl-2-ethylhexylammonium), 3,3'-nona(oxyethylene)oxy-bis(2-hydroxypropyldimethyloctylammonium), 3,3'-nona(oxyethylene)oxy-bis(2-hydroxypropyldimethyldecylammonium), and 3,3'-nona(oxyethylene)oxy-bis(2-hydroxypropyldimethylbenzylammonium).

Examples of the alkyl quaternary ammonium of the formula (1) where R2 is a substituent represented by the formula (2) and k is 13 include: 3,3'-trideca(oxyethylene)oxy-bis(2-hydroxypropyldimethylhexylammonium), 3,3'-trideca(oxyethylene)oxy-bis(2-hydroxypropyldimethyl-2-ethylhexylammonium), 3,3'-trideca(oxyethylene)oxy-bis(2-hydroxypropyldimethyloctylammonium), 3,3'-trideca(oxyethylene)oxy-bis(2-hydroxypropyldimethyldecylammonium), and 3,3'-trideca(oxyethylene)oxy-bis(2-hydroxypropyldimethylbenzylammonium).

Examples of the alkyl quaternary ammonium of the formula (1) where R2 is a substituent represented by the formula (2) and k is 22 include: 3,3'-docosa(oxyethylene)oxy-bis(2-hydroxypropyldimethylhexylammonium), 3,3'-docosa(oxyethylene)oxy-bis(2-hydroxypropyldimethyl-2-ethylhexylammonium), 3,3'-docosa(oxyethylene)oxy-bis(2-hydroxypropyldimethyloctylammonium), 3,3'-docosa(oxyethylene)oxy-bis(2-hydroxypropyldimethyldecylammonium), and 3,3'-docosa(oxyethylene)oxy-bis(2-hydroxypropyldimethylbenzylammonium).

The quaternary ammonium as described above forms a fatty acid salt of an alkyl quaternary ammonium, together with a caproate ion, a caprylate ion, caprate ion or the like.

(where R1 is an alkyl group having a carbon number of 6-10 or a benzyl group, HX is a fatty acid having a carbon number of 6-10, and $X^-$ is a fatty acid ion having a carbon number of 6-10.)

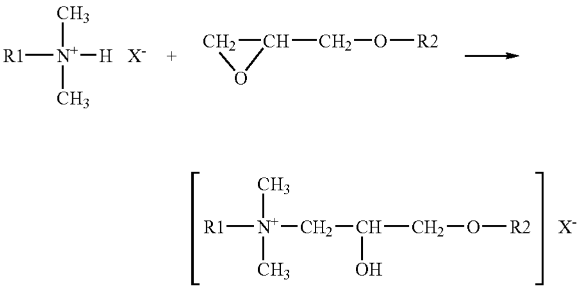

(where R1 is an alkyl group having a carbon number of 6-10 or a benzyl group, R2 is a hydrogen atom, a methyl group or a benzyl group, and $X^-$ is a fatty acid ion having a carbon number of 6-10.)

In the case of a quaternary ammonium salt of the formula (1) where R2 is a substituent represented by the formula (2), as shown in the formula before, the quaternary ammonium salt can be prepared by adding an (oxyethylene)$_k$ diglycidyl ether in the equimolar amount in terms of epoxy equivalent, to the produced fatty acid salt of the alkyldimethylamine, and stirring at room temperature to 80° C. for 1-10 hours.

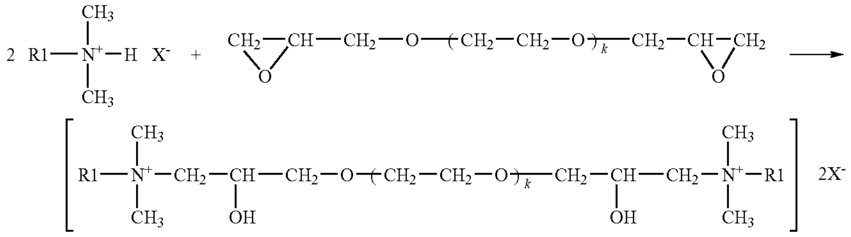

The quaternary ammonium salt represented by the formula (1) may be produced by, for example, the following method. Specifically, referring to formulae below, an alkyldimethylamine (tertiary amine) and a fatty acid in the equimolar amounts are mixed at room temperature using water as a solvent, to thereby produce a fatty acid salt of the alkyldimethylamine. Subsequently, to the produced fatty acid salt of the alkyldimethylamine is added a glycidyl alcohol or an alkyl glycidyl ether in the equimolar amount in terms of epoxy equivalent, and is stirred at room temperature (25° C.)-80° C. for 1-10 hours, to thereby prepare a quaternary ammonium salt.

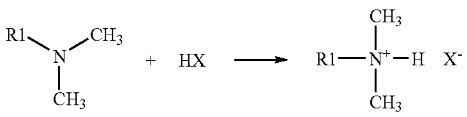

(where R1 is an alkyl group having a carbon number of 6-10 or a benzyl group, r is a fatty acid ion having a carbon number of 6-10, and k is an integer of 0-22.)

Examples of the alkyldimethylamine used for the production of the present surfactant include N,N-dimethylhexylamine, N,N-dimethylcaprylamine (N,N-dimethyloctylamine), and N,N-dimethyldecylamine, and these can be produced with methods known in the art.

Examples of the alkyl glycidyl ether include glycidyl methyl ether and benzyl glycidyl ether. Alkyl glycidyl ether and glycidyl alcohol can be produced with methods known in the art.

Examples of the (oxyethylene)$_k$ diglycidyl ether include oxyethylene diglycidyl ether (ethylene glycol diglycidyl ether), and dioxyethylene diglycidyl ether (diethylene glycol diglycidyl ether), and these can be produced with methods known in the art.

The present surfactant can be used as, for example, a wash fluid mixed with water. In this case, there is no specific limitation with respect to the present surfactant, but the present surfactant is preferably included in an amount of 0.05-5% by weight (% by mass), more preferably 0.1-5% by weight of the wash fluid.

The wash fluid containing the present surfactant mixed with water can be applied to, for example, washing of metal members, such as iron and steel product. Examples of washing of metal members include: washing for removing working fluid or the like attached to a surface of a metal member during a cutting process or the like, for the purpose of coating the surface with an aqueous solution, such as anti-carburization agent, before performing heat treatment, such as quench hardening; washing for removing quenching oil used during heat treatment; and washing for removing the anti-carburization agent after heat treatment or removing shot dust, steel balls or the like after shot blasting treatment.

With respect to washing method to which the present surfactant can be applied, there is no specific limitation, and examples include spray washing, soak washing, electrolytic washing and vibration washing. In any washing methods, the present surfactant exerts higher detergency and lower foaming property, as compared with the conventional surfactant. In the case of spray washing of metal members or the like, where foaming of the wash fluid might otherwise be notable, the present surfactant is expected to provide a remarkable effect of suppressing foaming, as a preferable composition for spray washing.

It should be noted that, in the present surfactant, R1 and $X^-$ in the formula (1) exhibit lower lipophilicity and thus lower detergency, when the carbon number is small. On the other hand, it is considered that a foam generated during washing has a double structure with hydrophobic groups (alkyl groups) located outside and hydrophilic groups located inside, and accordingly, when the alkyl group has a smaller carbon number, stability of foam becomes poor to lead collapse of foam, resulting in a higher suppression effect against foaming. Therefore, each of R1 and $X^-$ exerts the most effective performance when the carbon number is 6-10.

Since fatty acid generally has a higher acid dissociation constant (pKa) than that of carbonic acid, fatty acid tends to form a salt with an organic or inorganic cation prior to carbonic acid. Accordingly, by using the present surfactant, dissolved carbon dioxide hardly forms carbonate, to thereby prevent defects, such as white powder and blemish, which may otherwise be formed by remaining carbonate on the surface of the metal member or the like after washing.

With respect to the temperature at which the present surfactant is used during washing, there is no specific limitation, and any temperature can be selected. In general, detergency (such as degreasing power) improves when a wash fluid containing a surfactant is heated. On the other hand, when used at a normal temperature of 5-35° C., detergency decreases and foaming of the wash fluid becomes notable. In the case of the present surfactant, it is preferred that the surfactant is used at 50-90° C., but it is still preferred that the present surfactant is used at a normal temperature, since high detergency and low foaming property can be retained. In other words, in the case of the present surfactant, there is no limitation for working temperature, and for example, in the case of a factory where both a high-temperature washing process (washing at 50-90° C.) and a low-temperature washing process (washing at a normal temperature of 5-35° C.) are performed, the same washing fluid containing the present surfactant is used in the both washing processes, to thereby save the labor, such as managing the wash fluid.

The present surfactant may be used alone, but also used as a washing composition also containing a chelating agent, an alkaline agent or the like. Such a washing composition can be used as, for example, a wash fluid mixed with water. In this case, there is no specific limitation for the washing composition, but it is preferred that the washing composition include the present surfactant in an amount of 0.05-5% by weight, the chelating agent in an amount of 0.02-3% by weight, the alkaline agent in an amount of 0.05-5% by weight of the wash fluid.

The alkaline agent enhances detergency by interacting with the surfactant, and improves wettability, permeability and the like of the smudge to the wash fluid, by solubilizing the smudge through a reaction in the wash fluid to disperse the smudge, as well as by reducing a critical micelle concentration and surface tension of the surfactant. The chelating agent enhances a washing effect by dissolving an oxide film present at an interface between a clean surface of the metal member and the smudge, into the wash fluid, and at the same time, imparts brightness to the washed substance. Since the chelating agent retains pH of the wash fluid in a range of 9-11, an increase in the dissolved carbon dioxide from air can be suppressed, which prevents a formation of carbonate, to thereby prevents defects, such as white powder and blemish, which may otherwise be formed by deposition of carbonate on the surface of the metal member or the like.

Examples of the chelating agent include an aminocarboxylic acid type chelating agent and a polycarboxylic acid type chelating agent.

Examples of the aminocarboxylic acid type chelating agent include a chelating agent represented by the formula (3):

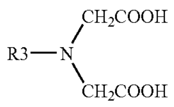

(3)

(where R3 is a hydrogen atom, an alkyl group having a carbon number of 1-4, a hydroxyalkenyl group having a carbon number of 1-4, or a substituent represented by the following formula (4):

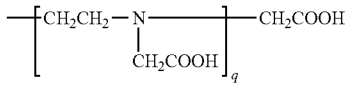

(4)

and q is an integer of 0-3). Specific examples include ethylenediamine tetraacetic acid, diethylenetriamine pentaacetic acid, nitrilotriacetic acid, and L-asparagine acid-N,N-diacetate.

Examples of the polycarboxylic acid type chelating agent include a polymer or copolymer of citric acid, tartaric acid, malic acid, acrylic acid or maleic acid, and specific examples include an aqueous polymeric carboxylic acid compound represented by the following formula (5):

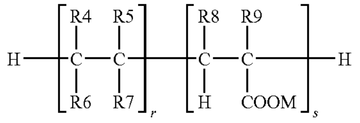

(5)

(where each of R4-R9 is a hydrogen atom, an alkoxyl group having a carbon number of 1-5, a carboxyl group, or a hydroxyl group, M is a hydrogen atom, an alkylamine having a carbon number of 1-4, or an alkanolamine having a carbon number of 1-6; r/s (copolymerization molar ratio) is 0/10-10/1; and an average molecular weight is 1,000-100,000).

It should be noted that these chelating agents are known compounds, and may be produced with methods known in the art. Alternatively, they may be commercially available products.

With respect to the alkaline agent, any alkaline agent such as inorganic alkaline agent and organic alkaline agent can be used without limitation, and examples include:

an alkanolamine represented by the following formula (6):

$$H_{3-m}N((R^{10}OH)_m \quad (6)$$

(where R10 is an alkylene group having a carbon number of 2 or 3, and m is an integer of 1-3), specifically, monoethanolamine, diethanolamine, triethanolamine, monoisopropanolamine, diisopropanolamine, and triisopropanolamine;

an ethyleneamine represented by the following formula (7):

$$H_2N(CH_2CH_2NH)_nH \quad (7)$$

(where n is an integer or 1-5), specifically, ethylenediamine, diethylenetriamine, and triethylenetetramine;

an alkoxyalkylamine represented by the following formula (8):

$$H_{3-t}N(R^{11}OR^{12})_t \quad (8)$$

(where $R^{11}$ is an alkylene group having a carbon number of 2 or 3, $R^{12}$ is an alkyl group having a carbon number of 1-3, and t is an integer of 1-3), specifically, methoxypropylamine and ethoxypropylamine;

an alkylamine represented by the following formula (9):

$$R^{13}NH_2 \quad (9)$$

(where $R^{13}$ is an alkyl group having a carbon number of 4-10), specifically, octylamine and decylamine; and a polyethyleneimine represented by the following formula (10):

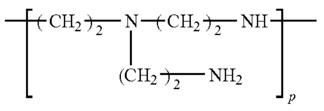

(10)

(where p is an integer which gives a molecular weight of 300-7,000).

It should be noted that these alkaline agents are known compounds, and can be produced with methods known in the art. Alternatively, they may be commercially available products.

To the wash fluid containing the present surfactant, there can be added an ether type nonionic surfactant, such as oxyethylene-oxypropylene block polymer, and polyoxyalkylene alkyl ether; an ampholytic surfactant, such as amine oxide; and other builders known in the art; in such amounts that they do not hinder the effect of the present invention.

EXAMPLES

The present invention will be described in more detail below with reference to examples in which the present invention is implemented. However, it should not be construed that the present invention is limited to these examples.

The present surfactant was prepared in the following manner. In a 500 ml four-neck flask were put 100 g (5.6 mol) of water, 15.7 g (0.1 mol) of N,N-dimethylcaprylamine, and 14.4 g (0.1 mol) of caprylic acid. While the mixture was stirred at room temperature, 15 g (0.05 mol) of diethylene glycol glycidyl ether was added, and the mixture was further stirred at 30-80° C. for approximately 6 hours, to thereby obtain a salt of 3,3'-di(oxyethylene)oxy-bis(2-hydroxypropyldimethyloctyl ammonium) caprylic acid, which is an ammonium salt represented by the formula (1) where $R^1$ is an n-octyl group (capryl group), $R^2$ is a substituent represented by the formula (2) and k is 2, and $X^-$ is caprylic acid.

Other fatty acid salts of alkyl quaternary ammonium were also prepared in substantially the same manner.

The present surfactant, monopropanolamine as the alkaline agent and ethylenediamine tetraacetic acid as the chelating agent, with concentrations as shown in Table 1, were mixed in water to thereby prepare a wash fluid. Using the prepared wash fluid, washing was performed under conditions shown in Table 2, and then detergency and foaming property were evaluated. The results are shown in Table 3.

For the detergency, residual oil on a washed substance after washing was measured with an oil content measuring device (OCMA-350 manufactured by HORIBA, Ltd.). For the wash fluid giving the residual oil content of less than 7.0 mg was categorized as "A", 7.0-8.0 mg as "B", and 8.0 mg or more as "C". The foaming property was evaluated in accordance with "JIS (Japanese Industrial Standards) K-3362.8.5e (Foaming property and foam stability)", and a foam height of 2 mm or less is categorized as "A", 2-5 mm as "B", and 5 mm or more as "C".

For comparison, surfactants represented by the formula (1) where R1 and $X^-$ do not fall in the ranges as defined for the present surfactant, as well as the conventional surfactants, were used. Detergency and foaming property are evaluated in substantially the same manner as described above, and the results are shown in Table 4. A conventional product A is a wash fluid mainly composed of alkylamine oxide, a conventional product B is a wash fluid mainly composed of polyoxyethylene, a conventional product C is a wash fluid mainly composed of polyoxyethylene polyoxypropylene glycol, a conventional product D is a wash fluid mainly composed of a special alkyl phosphate, and a conventional product E is a wash fluid mainly composed of polyoxyethylene paracumylphenyl ether.

As a result, it was confirmed that both high detergency and low foaming property can be attained only in the case of the surfactant of the formula (1) where R1 is an alkyl group having a carbon number of 6-10 or a benzyl group and $X^-$ is a fatty acid ion having a carbon number of 6-10.

TABLE 1

| Wash fluid composition | |
|---|---|
| Present surfactant | 0.5% by weight |
| Monoisopropanolamine | 1.0% by weight |
| Ethylenediamine tetraacetic acid | 0.5% by weight |

TABLE 2

| Washing conditions | |
|---|---|
| Washing equipment | Spray washer |
| Wash fluid concentration | 5% by weight |
| Liquid temperature | Normal temperature (25 ± 1° C.), 60 ± 1° C. |
| Washing time | 20 seconds |
| Spray pressure | 0.8 MPa |
| Washed substance | Front sun gear |

TABLE 3

| R1 (C number) | R2 | k | $X^-$ (C number) | Detergency Normal temperature | Detergency 60° C. | Foaming property Normal temperature | Foaming property 60° C. |
|---|---|---|---|---|---|---|---|
| 6 | Formula (2) | 2 | 6 | A | A | A | A |
| 6 | Formula (2) | 1 | 8 | A | A | A | A |
| 6 | $CH_2Ph$ | — | 8 | A | A | A | A |
| 6 | Formula (2) | 2 | 10 | A | A | B | A |
| 8 | Formula (2) | 2 | 6 | A | A | A | A |
| 8 | Formula (2) | 2 | 8 | A | A | A | A |
| 8 | $CH_3$ | — | 8 | A | A | A | A |
| 8 | Formula (2) | 2 | 10 | A | A | B | A |
| 10 | Formula (2) | 1 | 6 | A | A | A | A |
| 10 | Formula (2) | 2 | 8 | A | A | A | A |
| 10 | Formula (2) | 1 | 10 | A | A | A | A |
| 10 | H | — | 10 | A | A | B | A |
| $CH_2Ph$ | Formula (2) | 2 | 6 | A | A | A | A |
| $CH_2Ph$ | Formula (2) | 1 | 8 | A | A | A | A |
| $CH_2Ph$ | Formula (2) | 2 | 10 | A | A | A | A |

TABLE 4

| R1 (C number) | R2 | k | $X^-$ (C number) | Detergency Normal temperature | Detergency 60° C. | Foaming property Normal temperature | Foaming property 60° C. |
|---|---|---|---|---|---|---|---|
| 4 | Formula (2) | 2 | 4 | C | C | A | A |
| 4 | Formula (2) | 1 | 6 | C | C | A | A |
| 4 | Formula (2) | 1 | 8 | C | B | A | A |
| 4 | Formula (2) | 1 | 10 | C | B | B | A |
| 4 | Formula (2) | 2 | 12 | A | A | C | C |
| 6 | Formula (2) | 1 | 4 | C | C | A | A |
| 6 | Formula (2) | 2 | 12 | A | A | C | C |
| 8 | Formula (2) | 2 | 4 | C | B | A | A |
| 8 | Formula (2) | 1 | 12 | A | A | C | C |
| 10 | Formula (2) | 2 | 4 | C | B | A | A |
| 10 | Formula (2) | 2 | 12 | A | A | C | C |
| 12 | Formula (2) | 2 | 4 | C | B | C | C |
| 12 | Formula (2) | 1 | 6 | A | A | C | C |
| 12 | Formula (2) | 2 | 8 | A | A | C | C |
| 12 | Formula (2) | 2 | 10 | A | A | C | C |
| 12 | Formula (2) | 2 | 12 | A | A | C | C |
| $CH_2Ph$ | Formula (2) | 2 | 4 | C | C | A | A |
| $CH_2Ph$ | Formula (2) | 2 | 12 | A | A | C | C |
| | Conventional product A | | | B | B | B | A |
| | Conventional product B | | | B | B | C | C |
| | Conventional product C | | | C | C | A | A |
| | Conventional product D | | | C | B | B | B |
| | Conventional product E | | | C | B | C | B |

INDUSTRIAL APPLICABILITY

The surfactant of the present invention can be used for, for example, washing metal members.

The invention claimed is:

1. A surfactant represented by the following formula (1):

(1)

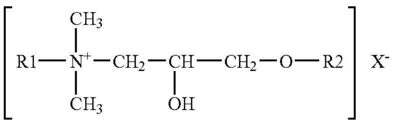

(where R1 is an alkyl group having a carbon number of 6-10 or a benzyl group,

R2 is a hydrogen atom, a methyl group, a benzyl group or a substituent represented by the following formula (2):

(2)

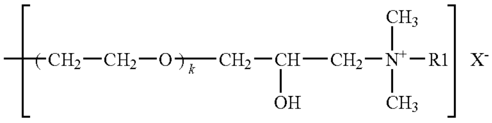

$X^-$ is a fatty acid ion having a carbon number of 6-10, and k is an integer of 0-22).

2. The surfactant according to claim 1, wherein R1 is selected from the group consisting of an n-hexyl group, an n-octyl group and an n-decyl group.

3. The surfactant according to claim 1, wherein $X^-$ is selected from the group consisting of a caproate ion, a caprylate ion and a caprate ion.

4. A composition for spray washing comprising a surfactant according to claim 1.

* * * * *